United States Patent [19]

Kallos et al.

[11] Patent Number: 5,538,643
[45] Date of Patent: Jul. 23, 1996

[54] CONTINUOUS FLOW APPARATUS AND METHOD FOR INTERFACING LIQUID CHROMATOGRAPH AND FOURIER TRANSFORM INFRARED SPECTROMETER

[75] Inventors: George J. Kallos, Saginaw; Richard R. Papenfuss, Midland, both of Mich.

[73] Assignee: The Dow Chemical Company, Midland, Mich.

[21] Appl. No.: 434,306

[22] Filed: May 2, 1995

Related U.S. Application Data

[63] Continuation of Ser. No. 170,313, Jun. 3, 1994, and a continuation-in-part of Ser. No. 738,769, Aug. 1, 1991, abandoned.
[51] Int. Cl.$^6$ ...................................................... B01D 15/08
[52] U.S. Cl. .................................... 210/656; 210/198.2
[58] Field of Search ............................... 210/656, 198.2; 250/288 A

[56] References Cited

U.S. PATENT DOCUMENTS

| | | | |
|---|---|---|---|
| 4,883,958 | 11/1989 | Vestal | 250/288 |
| 4,968,885 | 11/1990 | Willoughby | 250/288 |
| 5,285,064 | 2/1994 | Willoughby | 250/288 |

*Primary Examiner*—Frank Spear
*Attorney, Agent, or Firm*—Timothy S. Stevens

[57] ABSTRACT

Apparatus for interfacing a liquid chromatograph (LC) with a spectrometer such as a Fourier transform infrared spectrometer, the LC having an eluant, the eluant containing a solvent and a component of interest. The apparatus includes five basic parts. The first is a means for generating a stream of droplets of the eluant, such as a nebulizer. The second is a means for removing most of the solvent from the stream of droplets of the eluant to thereby generate a stream of particles, the particles containing the component of interest and any residual solvent, such as a membrane solvent separator/momentum separator combination. The third is a cryogenic receiving surface, such as a gold drum. The forth is a means for focusing the stream of particles onto the cryogenic receiving surface so that the particles adhere to the cryogenic receiving surface, such as a one and two-tenths millimeter inside diameter stainless steel tube positioned with a gap between the distal end of the tube and the cryogenic receiving surface of one-quarter millimeter. The fifth is a means for controlling the temperature of the cryogenic receiving surface, such as a helium refrigerator. In operation, the cryogenic receiving surface is maintained at a temperature effective to cause the particles to adhere to the cryogenic receiving surface to form a region of adhered particles, such as a temperature of between seventy and one hundred and five degrees Kelvin, the cryogenic receiving surface being maintained in a partial vacuum. Then, the cryogenic receiving surface is warmed, e.g., to between one hundred and five and two hundred degrees Kelvin, to volatilize essentially all of any remaining solvent from the region of adhered particles prior to spectroscopic analysis of the region of adhered particles.

10 Claims, 11 Drawing Sheets

CONTINUOUS FLOW APPARATUS AND METHOD FOR INTERFACING LIQUID CHROMATOGRAPH AND FOURIER TRANSFORM INFRARED SPECTROMETER

CROSS-REFERENCE TO RELATED APPLICATION

This is a continuation of application Ser. No. 08/170,313, filed Jun. 3, 1994, now abandoned which is a 371 of PCT/US 92/06341 filed Jul. 30, 1992 on a CIP Ser. No. 07/738,769, filed Aug. 1, 1991, now abandoned

TECHNICAL FIELD

This invention relates to an apparatus and method for interfacing a liquid chromatograph with a fourier transform infrared spectrometer which is applicable to continuous flow use in, e.g., both normal phase and reverse phase separations, and, more particularly, to an improved apparatus and method for removing solvent from continuous flow liquid chromatograph eluent and collecting the sample particles thereby generated for reliable and accurate infrared spectroscopy.

BACKGROUND ART

The high degree of compound selectivity made possible by combining liquid chromatography with molecular detector methods which provide structural information has been recognized as extremely valuable for the identification of various components of complex mixtures. Particularly, liquid chromatographs (LC), and especially high-performance liquid chromatographs (HPLC), have proven to be excellent means for separating a mixture and determining the individual constituents, either quantitatively or volumetrically. However, LC and HPLC devices have the disadvantage that they do not satisfactorily identify the separated constituents.

On the other hand, the mass spectrometer (MS) is extremely capable and sensitive in identifying single components, while having considerable difficulty in identifying a mixture. Consequently, hybrid techniques which combine chromatography with molecular methods such as mass spectrometry and fourier transform infrared spectrometry have been developed and are used extensively for component analysis in complex mixtures.

The high scan speed and sensitivity of fourier transform infrared (FTIR) spectroscopy have enabled the recording of infrared spectra of individual components of a mixture which have been separated by chromatographic techniques. Coupling of FTIR equipment has been successfully accomplished for gas chromatography (GC), however, many compounds and mixtures are not sufficiently volatile for GC separation. Moreover, the sensitivity of a combination GC/FTIR mechanism is reduced for less volatile compounds, making this combination unacceptable. Particularly, the less volatile and/or more polar compounds must usually be separated by HPLC.

Interfacing of LC mechanisms with FTIR devices has not been substantially successful heretofore due to the infrared absorption of the mobile phase of the HPLC eluent. Generally, solvents which are good mobile phases for LC and HPLC applications are also usually strong infrared absorbers. To address this problem, two general types of systems have been developed; (1) flow cells which take advantage of some mobile phases which have large IR windows; and (2) elimination of the mobile phase prior to deposition of the eluate on an appropriate substrate. Each of these approaches, however, have their own problems in achieving a reliable and universal interface arrangement.

For example, all solvents absorb some infrared radiation, and the degree of such absorption defines the maximum path length which a flow cell can have which will allow identifiable spectra to be obtained. Additionally, mobile phases having large IR windows are generally of low polarity and are used only for normal-phase HPLC. The shorter path lengths which must be used to minimize interference resulting from mobile phase absorption similarly limit the volume of the flow cell, thereby limiting the concentration of the analyte being measured at any one instant, and compromising the accuracy of the process overall. The major challenge of interfacing normal-phase and reverse-phase HPLC to IR techniques is the incompatibility of typical solvents to identification of unknown constituents by IR technology. Consequently, water and other typical mobile phases used in LC separations are best eliminated prior to measuring the IR spectrum of a component.

A variety of methods and devices have been directed toward eliminating solvents prior to FTIR procedures, including flowing effluent from a capillary HPLC column into a stainless steel wire net designed to eliminate the solvent as a result of a heated gas flow. Particularly, the sample material was to be suspended between the metal meshing, and the deposits were then analyzed. Griffiths et al. developed a system wherein the HPLC effluent is deposited on an IR transparent substrate as warm nitrogen induces solvent evaporation prior to IR analysis. An interface where deposition of the sample material was to be continuous was developed by Gagel and Biemann, where effluent from a microbore HPLC was continuously sprayed on a rotating disk as warm nitrogen was passed across the disk to evaporate the solvent. In that procedure, however, the FTIR spectra were measured off-line by fastening the collection device to a reflectance accessory.

A solvent removal interface developed by Kalasinsky for reverse phase HPLC contemplated the elimination of water by employing a particular chemical (2,2'-dimethoxypropane) to convert the water to methanol and acetone for deposition on a KCl substrate. Such conversion requires specific matching of chemicals and collection substrates, and does not truly remove the solvent but merely converts it to other substances which can independently add interference to analysis results. Browner and coworkers developed a monodisperse aerosol generator interface for combining LC and FTIR spectrometry, known as the MAGIC interface. With this interface, mobile phase elimination was to be accomplished at room temperature, wherein effluent from an HPLC enters the interface through a 25 micrometer diameter orifice to form a liquid jet. The jet is dispersed by a Helium (He) stream to create a fine aerosol which is directed from a desolvation chamber into first and second momentum separators. In the first momentum separator, evaporated solvent and Helium are removed by vacuum pumps, and the nonvolatile analyte continues into the second momentum separator where any residual volatile material is to be removed. The nonvolatile analyte is then deposited on a KBr (potassium bromide) window which is removed and placed in a beam condenser for IR analysis. Because the solvent is eliminated prior to deposition on the substrate, the isolated analyte can be deposited on a variety of substrates for various IR detection methods.

In U.S. Pat. Nos. 4,814,612 and 4,883,958, M. L. Vestal, et at. described similar apparatuses and methods for coupling LC and solid phase detectors, including the use of thermospray vaporizers which vaporize most of the solvent prior to introduction to a desolvation chamber. The device set forth in the '958 patent further contemplates passing the vaporized solvent and added carrier gas through one or more solvent removal chambers, which can remove solvent by condensation or diffusion through a membrane to a counterflowing gas stream. This device may further include a momentum separator to concentrate particles relative to the remaining solvent vapor and carrier gas, and teaches the direction of a particle beam for impact with a cryogenically cooled deposition surface. In the Vestal '612 patent, a moving belt is provided for receiving the particle beam, and a temperature transducer is positioned adjacent the belt to maintain the belt at a temperature where no significant amount of the particle sample will be vaporized, yet warm enough that residual liquid solvent is vaporized efficiently in a stream of counterflowing gas which passes over the belt.

The Vestee Universal Interface incorporates many of the features described in the Vestal patents mentioned above, and is available in the industry from Vestec Corporation of Houston, Tex.

An apparatus for combining LC technology with mass spectrometry is described in U.S. Pat. No. 4,980,057, which issued to S. B. Dorn, et al. The Dorn, et al. device includes a nebulizer which volatilizes the LC eluate to form an aerosol which passes through a desolvation chamber. The nebulizer introduces an inert gas which helps vaporize the solvent and carries the aerosol to a momentum separator which accelerates the particles to sonic velocities. The momentum separator includes three vacuum pumping stages, wherein the first two stages are defined by conical skimmer nozzles, and the third chamber includes a long inlet tube which provides the vacuum pumping restriction. The resulting particle beam is provided to the MS ion source for analysis.

Consequently, while a great number of investigations and techniques have been attempted heretofore, LC/FTIR interfaces have provided only limited success in providing interpretable IR spectra from normal-phase and reverse-phase separations, due to inadequate solvent elimination and/or limited applicability to IR analysis.

DISCLOSURE OF THE INVENTION

It is an object of this invention to provide an improved apparatus and method for interfacing a liquid chromatograph with a fourier transform infrared spectrometer.

It is another object of the present invention to provide an improved LC/FTIR interface which provides continuous flow collection and analysis of sample compounds.

It is yet another object of the present invention to provide an apparatus and method which is effectively universal in interfacing LC and FTIR technology in a reliable and accurate manner for both normal-phase and reverse-phase separations.

It is also an object of the present invention to provide an LC/FTIR interface which features improved elimination of solvent from the LC eluent, and improved concentration of the particle beam for deposition and analysis.

It is another object of the present invention to provide an improved method for interfacing LC and FTIR analyzers, and for continuously collecting particle beam data for FTIR analysis under full normal flow operation of the LC separator.

In accordance with one aspect of the present invention, there is provided an apparatus for interfacing a liquid chromatograph (LC) with a spectrometer such as a Fourier transform infrared spectrometer, the LC having an eluant, the eluant containing a solvent and a component of interest. The apparatus include five basic parts. The first is a means for generating a stream of droplets of the eluant, such as a nebulizer. The second is a means for removing most of the solvent from the stream of droplets of the eluant to thereby generate a stream of particles, the particles containing the component of interest and any residual solvent, such as a membrane solvent separator/momentum separator combination. The third is a cryogenic receiving surface, such as a gold drum. The forth is a means for focusing the stream of particles onto the cryogenic receiving surface so that the particles adhere to the cryogenic receiving surface, such as a one and two-tenths millimeter inside diameter stainless steel tube positioned with a gap between the distal end of the tube and the cryogenic receiving surface of one-quarter millimeter. The fifth is a means for controlling the temperature of the cryogenic receiving surface, such as a helium refrigerator. In operation, the cryogenic receiving surface is maintained at a temperature effective to cause the particles to adhere to the cryogenic receiving surface to form a region of adhered particles, such as a temperature of between seventy and one hundred and five degrees Kelvin, the cryogenic receiving surface being maintained in a partial vacuum. Then, the cryogenic receiving surface is warmed, e.g., to between one hundred and five and two hundred degrees Kelvin, to volatalize essentially all of any remaining solvent from the region of adhered particles prior to spectroscopic analysis of the region of adhered particles.

BRIEF DESCRIPTION OF THE DRAWINGS

While the specification concludes with claims particularly pointing out and distinctly claiming the present invention, is believed the same will be better understood from the following description taken in conjunction with the accompanying drawings in which:

FIG. 10 is a phase sensitive IR reconstructed chromatogram of the polymer additives mixture plotted in. FIG. 9, but utilizing a capillary inlet tube having a tip inside diameter of 0.5 mm, wherein relative concentration is plotted on the vertical axis against retention time (in minutes) on the horizontal axis;

DETAILED DESCRIPTION OF THE INVENTION

Figure 1:
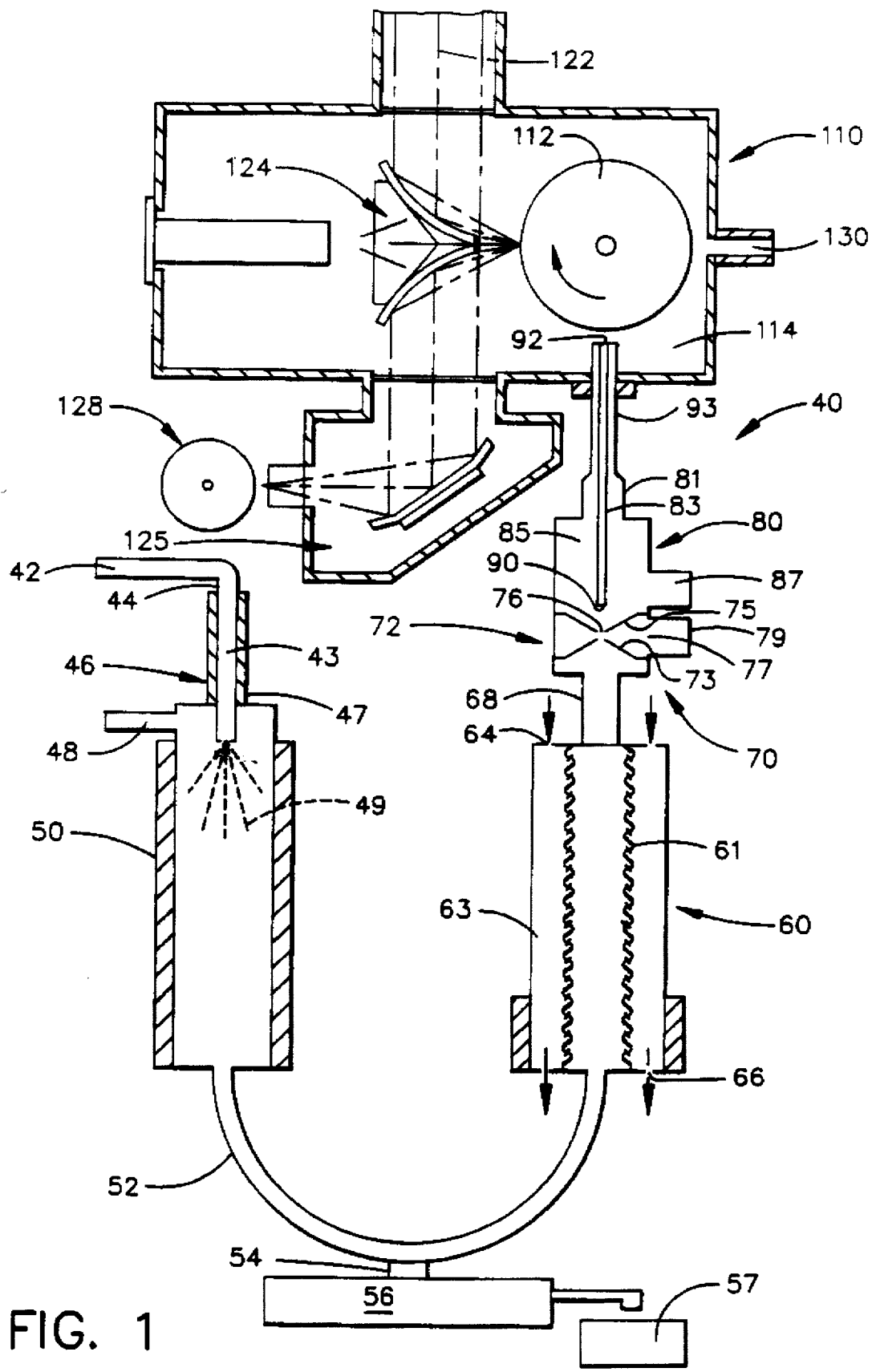
FIG. 1 is a schematic illustration of an apparatus for interfacing a liquid chromatograph with a fourier transform infrared spectrometer made in accordance with the present invention.

Referring now to the drawings in detail, wherein like numerals indicate the same elements throughout the views, FIG. 1 is a schematic illustration of an apparatus 40 for interfacing a liquid chromatograph (LC) device (e.g., 42) with a fourier transform infrared spectrometer (FTIR) device (e.g., 110). Particularly, an LC effluent line 44 directly connects a standard chromatographic column of LC device 42 with interface apparatus 40, extending inwardly into desolvation chamber 50 in the form of a thermospray vaporizer 46. Thermospray vaporizers are well known in the industry, such as available from Vestee Corporation, Houston, Tex. A heating means 47 may preferably circumscribe a portion of effluent line 44 and/or comprise part of vaporizer 46 to facilitate vaporization of the solvent included in effluent 43 passing therethrough.

The nebulized LC eluent 43 is entrained with an inert carrier gas, such as Helium (He), which is introduced via inlet 48 adjacent the upper portions of desolvation chamber 50. The entrained aerosol 49, i.e., a stream of droplets of the eluant, is thereby carried along desolvation chamber 50 and into carrier tube 52, and the flow rate of the incoming eluent 43 will preferably match the standard chromatographic column flow up to about 2 ml/minute or more.

A generally U-shaped portion of carrier tube 52 enables collection of condensate from the vaporized solvent for removal via peristaltic pump 56 through vent 54, and deposition in waste collection device 57. Carrier tube 52 directs aerosol 49 to membrane separator 60, which comprises a membrane 61 serially connected with carrier tube 52. The membrane should be sufficiently permeable that the solvent vapor can diffuse freely across it, yet provide a sufficient barrier to flow of carrier gas such that any net flow of gas through the membrane is relatively small. In this way, sample particles to be analyzed will not pass through the membrane, and the membrane can effectively extract solvent vapor from aerosol 49. As set forth in U.S. Pat. No. 4,883,958, a fibrous porous form of PTFE available under the tradename "Zitex" has been found to be satisfactory for use as membrane 61. A gas diffusion cell 63 effectively surrounds membrane 61 to contain a counterflow gas stream provided by gas inlet 64 and outlet 66. It is preferred that this counterflow gas also be inert, and identical to the carrier gas utilized in the system.

The dry aerosol issuing from membrane separator 60 continues through a reduced diameter section 68 of carrier tube 52 into momentum separator 70, situated downstream from membrane separator 60. Reduced section 68 can preferably comprise a Teflon™ tube having an inside diameter of approximately 6.25 min. While membrane separator 60 can efficiently operate at substantially atmospheric pressure, momentum separator 70 is provided with a pair of first and second pumping stations 72 and 80 respectively, each provided with a source of underpressure or vacuum.

Particularly, the dry aerosol from membrane separator 60 continues toward momentum separator 70 as a result of the momentum of the carrier gas being supplied via inlet 48, and as a result of being pulled by the underpressure present in interior 77 of first pumping stage 72. Such underpressure or vacuum is provided to first pumping stage 72 via vacuum fitting 79 which is connected to an appropriate pump (not shown). Interior 77 is defined by inlet nozzle 73 and conical skimmer device 75 having an opening 76 of predetermined diameter. Pressure within interior 77 may be set at an appropriate underpressure of approximately 500 Torr. By such differential pumping, the carrier gas and remaining evaporated solvent is removed from the aerosol as it passes within interior 77 toward second pumping stage 80.

The de-gassed dry aerosol exiting first pumping stage 72 passes through opening 76 into second pumping stage 80 as a result of its momentum, and due to a relatively greater underpressure within interior 85 of second stage 80. Conical skimmer 75 and a capillary inlet tube 83 having an inside diameter of approximately 1.2 mm effectively isolate second stage 80 from first pumping stage 72 and from the vacuum chamber 114 (and source) of FTIR device 110. Fitting 87 connects interior 85 to a second vacuum pump (not shown) which provides a relatively more significant underpressure (e.g., approximately 0.5 Torr) within second stage 80, and enables removal of residual carrier gas and vaporized solvent passing within interior 85. Upon removal of substantially all of the carrier gas and remaining vaporized solvent, aerosol 49 has been effectively transformed into a beam or stream of sample particles of the sample compound, i.e., of the component of interest.

Due to the momentum of the particle beam, and an even more severe underpressure or vacuum within FTIR device 110, the particle beam continues its movement into capillary orifice 90, through tube 83, and out distal end 92 thereof. In this way, the particle beam is directed from capillary tube 83 and collimated, i.e, focused, onto a cryogenic collection disk or drum 112, i.e., onto a cryogenic receiving surface, within the interior or vacuum chamber 114 of the cryogenic chamber of FTIR device 110. Preferably, the focusing results in a deposit of particles having a small area so that sensitivity of detection is maximized and so that chromatographic resolution is maintained. It is preferred that collection disk 112 be provided with a rotary stage 115 to enable rotation for continuous collection and IR analysis. It has been found that interface apparatus 40 can enable a pressure of $5.4 \times 10^{-5}$ Torr within chamber 114. Particles collected upon collection disk 112 can thereafter be analyzed by IR detector 128, with optical beam 122 being focused by mirrors 124 and 125 onto rotating collection disk 112, as illustrated. Further details of FTIR device 110 will be omitted herein, 8s commercial FTIR devices such as the Cryolect 4800™ (manufactured by Mattson Instruments, Inc. of Madison, Wis.) are commonly available in the industry.

Figure 2:
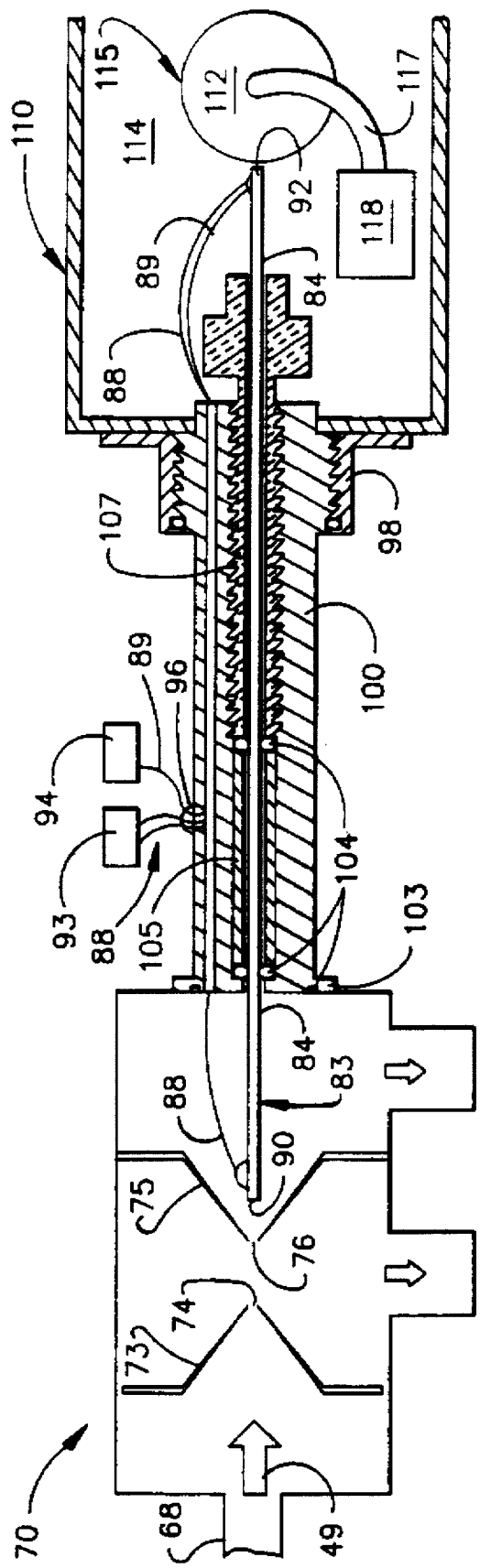
FIG. 2 is an enlarged schematic view of a preferred embodiment of a momentum separator of an interfacing apparatus made in accordance with the present invention.

It has also been found that heating of portions of the interface of the present invention is preferred to insure transfer of as much of the sample compound as possible to the cryogenic collection disk 112. In this regard, means for heating capillary tube 83 can be provided to minimize condensation or other collection of particles along tube 83 and prior to deposition on the collection disk. A preferred manner of providing such heating means comprises coating the outside diameter of a glass capillary tube 83 with a uniform, at least partially conductive material (e.g., silver epoxy as available from Epoxy Technology, Inc., Billericq, Mass.), and passing current along the coating to apply a controlled amount of heat thereto. For example, an 83 mm long tube 83 having an inside diameter of 1.2 mm coated with silver epoxy can be maintained at approximately 200° C. through the use of 8 volts AC power controlled through two variacs (e.g., see 93 of FIG. 2) as seen in FIG. 2, a thermocouple 94 can be provided to control heater 93 to provide proper electrical power through heating wires 88. On the other hand, if a metal tube 83 is used, then heating of the tube 83 is less important, e.g., a one-sixteenth inch outside diameter, one and two-tenths millimeter inside diameter stainless steel tube 83. Preferably the inside diameter of the tube 83 is between about one-half and about two millimeters and more preferably it is between about one and one and one-half millimeter. However, the inside diameter of the tube 83 can be smaller than one-half millimeter, e.g., one-quarter millimeter or one-eighth millimeter. On the other hand, the inside diameter of the tube 83 can be larger than two millimeters, e.g., four millimeters or eight millimeters.

The tube 83 is one means for focusing a stream of particles onto a cryogenic receiving surface, e.g., the disk 112. Another means for focusing a stream of particles onto a cryogenic receiving surface would be to replace the tube 83 with an aperture plate mounted just before the disk 112. In this case, it is preferable to reduce the spacing between the disk 112 and the skimmer 75. If the disk 112 were positioned adjacent the skimmer 75, then the skimmer 75 would serve as a means for focusing a stream of particles onto a cryogenic receiving surface. However, in this case, it would be more preferable to add an additional nozzle and pumping stage, like the nozzle 74, after the skimmer 75 and position the disk 112 very near the tip of the added nozzle.

Turning to the details of FIG. 2, momentum separator 70 may preferably be connected to FTIR device 110 via a link housing 100 sealed within flange 103 via an o-ring 104, and connected at its opposite end to adapter 98 attached adjacent cryogenic chamber 110. Heated capillary tube 83 passes through link housing 100, and is supported therein by a spacer 105, and a pair of O-rings 104. O-rings 104 also serve to insulate tube 83 so that it can be heated electrically. Heating wires 88 and thermocouple connection wire 89 are appropriately connected to capillary tube 83 through housing 100 and seal 96.

Cryogenic disk 112 is preferably provided with a rotary stage 115, and can be cooled via a source of liquid helium (not shown), such as through cooling line or cold finger 117. The use of a helium refrigerator arrangement to facilitate achieving and maintaining cryogenic temperatures is well known in the industry, and will not be further described herein. Of course, other refrigeration means can be used such as liquid nitrogen. A control device 118 may be provided to control the temperature and rotary motion of collection disk 112. Rotation of disk 112 may be desired to allow deposition of particles thereon in a spiral-like pattern to enable continuous deposition and analysis for extended periods of time.

Capillary tube 83 serves to collimate the particle beam so that the particles can be accurately targeted onto the cryogenic collection disk 112, either with or without a matrix gas such as argon. As mentioned above, if the tube 83 is made of glass, then tube 83 is preferably heated (e.g., to a temperature of about 130°–140° C. to help insure that sample particles do not condense or collect along the tube prior to deposition on disk 112. By accurately collimating and targeting the particle beam onto collection disk 112, the deposition of sample particles can be restricted to a relatively narrow spot on the disk, thereby concentrating the sample and optimizing the infrared spectrum obtainable therefrom. It has been found that sensitivity of an arrangement made in accordance with the present invention is superior, and has been measured in the range of between about 300 and 400 nanograms of material injected into the liquid chromatograph. The gap between the tip of the tube 83, or other such means, and the disk 112 is important. This gap is preferably between about one-eighth and about one millimeter and more preferably it is between about one-quarter and about one-half millimeter. However, this gap can be smaller than one-quarter millimeter, e.g., one-hundredth millimeter, one-fiftieth millimeter, one-twentyfifth millimeter or one-twelfth millimeter. On the other hand, this gap can be greater than one millimeter, e.g., two millimeters, four millimeters, eight millimeters or even more.

Collection disk 112 is to be maintained in a preferred temperature range of between about 70 K. and about 105 K. for collection of particles. While this range is not critical, it has been found that collection at temperatures significantly below 70 K. may result in cracking or flaking of the material deposited on the disk, as a result perhaps of inelasticity at the lower temperatures. It may be important not to remove absolutely all of the solvent from the stream of particles and the particles themselves prior to the particles impacting the cryogenic receiving surface. The residual solvent may be beneficial to "glue" the particles to the cryogenic receiving surface. However, it should be clearly understood that this is not known to be true at present. It is only hypothesized to help explain the invention and not to be limiting thereof. Similarly, because collection is undertaken in a vacuum atmosphere, (e.g., $5.4 \times 10^{-5}$ Torr, i.e., the term "vacuum" means a partial vacuum and not an absolute vacuum) collection above about 110 K. may run the risk of vaporizing some or all of some sample particles, thereby compromising the sensitivity and accuracy of the IR analysis. Components of interest such as high polymers are relatively free of this problem. Therefore, the temperature of the cryogenic receiving surface that is effective to cause the particles to adhere to the cryogenic receiving surface can be as low as two, four, eight, sixteen, thirty two, or sixty four degrees Kelvin or as high as one hundred fifty, two hundred, two hundred fifty or three hundred degrees Kelvin depending on the component of interest.

Collection of vapor phase compounds separated by a gas chromatograph onto a rotating disk is known in the industry, and has been documented by equipment suppliers such as Mattson Instrument, Inc. of Madison, Wis.

Following deposition and collection of sample particles on disk 112, the temperature of disk 112 is allowed to rise, e.g., to approximately 180 K. It has been found that relative warming of the disk following collection of the particles is beneficial to optimizing IR test analysis results, and serves to remove trace residual amounts of solvent both from the disk and compounds collected on the disk. Following warming the disk, e.g., to approximately 180 K., its temperature is then preferably cooled down to approximately 13 K., so that the drum 112 contracts into better focus of the light beam 122, prior to undertaking the IR spectroanalysis. As will be seen in the examples below, resulting IR analysis following this serial warming and cooling procedure is essentially noise free, with the base line between analyzed components in the compound dropping to approximately zero. Temperature controller 118 can automatically implement the required temperature profile of collection disk 112, such as by computer supervision or the like.

Once collection of particles and data acquisition has been completed, disk 112 can be cleaned by warming to room temperature, whereupon volatile particles will vaporize and can be extracted from chamber 110 via vacuum. Less volatile components may also require physical cleaning of the disk with solvent or the like.

EXAMPLES

Warming Procedure Omitted

An experiment utilizing the apparatus and method of the present invention described above was undertaken utilizing a mercury cadmium telluride liquid nitrogen cooled detector for phase sensitive IR chromatograms, based upon the result of averaging 10 interferograms using $4cm^{-1}$ resolution. The cryogenic collection disk was maintained between about 70 K. and 105 K., and the cryogenic chamber of the FTIR device operated at a working vacuum of approximately $8 \times 10^{-5}$ Torr. After the chromatography was completed, the temperature of the disk was allowed to rise to about 180 K., then cooled to 13 K. before obtaining the phase sensitive IR chromatogram and measuring the spectra of the separated components. Other conditions for this experiment include the following:

| Chromatographic and Interface Conditions | |
| --- | --- |
| Column: | 10 cm × 4.6 mm 3µC$_8$ |
| Solvent: | 76/24 Acetonitrile/Water |
| Flow Rate: | 1 ml/min |
| Detector: | 210 run |
| Inlet Interface Diameter: | 1.2 mm |
| Inlet Interface Temp.: | 138° C. |
| He Flow Carrier/Sweep: | 4/6.8 L/min. |
| Control: | 73° C. |
| Tip: | 138° C. |
| Chamber: | 66° C. |
| Membrane: | 31° C. |
| Momentum Separator: | 106° C. |
| Pressure First Stage: | 500 Torr |
| Pressure Second Stage: | 0.5 Torr |
| Cryo-Disk: | 70K–95K |
| Crya Vacuum: | $8 \times 10^{-5}$ Torr |

Figure 3:
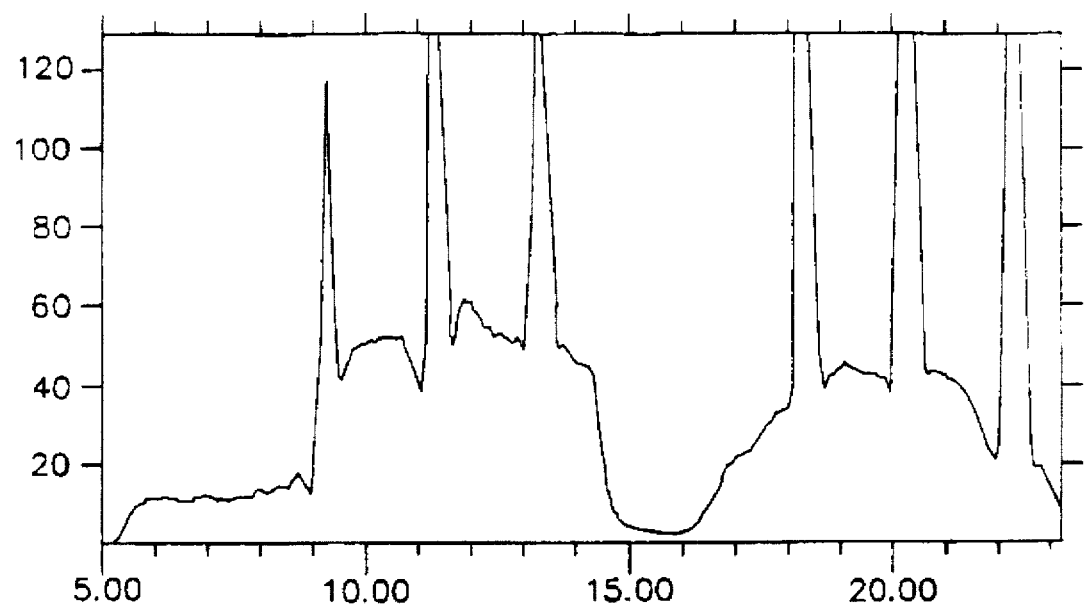
FIG. 3 is a phase sensitive IR reconstructed chromatogram of an infrared analysis of DOWCO™ 441 butyl ester and XRD-433 1-methyl heptyl ester sample mixture where the collection disk was not warmed prior to cooling and IR analysis, wherein relative concentration is plotted on the left axis against retention time (in minutes) on the horizontal axis.
Figure 4:
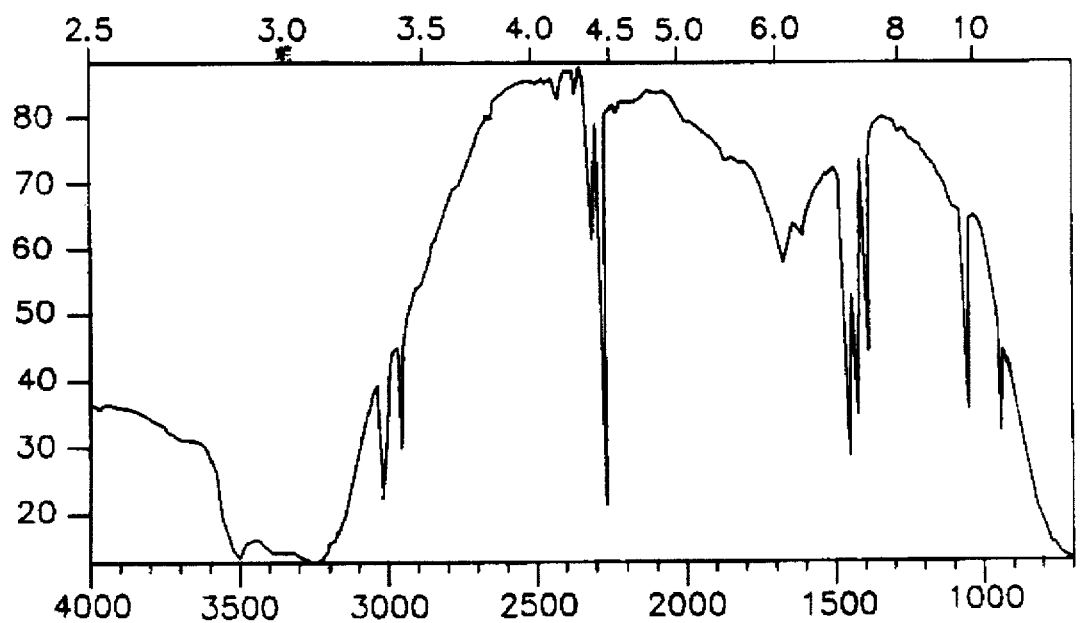
FIG. 4 is a single beam spectrum plot of one of the peaks of the chromatogram of FIG. 3 associated with DOWCO™ 441 butyl ester, wherein emissivity is plotted on the vertical axis against wavenumber along the lower horizontal axis, and wavelength (in microns) along the upper horizontal axis.

A mixture of XRD-433 1-methyl heptyl ester (43 ng/µl), and DOWCO™ 441 butyl ester (111 ng/µl) was flow injected into the liquid chromatograph and the column eluent collected in accordance with the present procedure. A graph showing the phase sensitive IR reconstructed chromatogram of this mixture is shown in FIG. 3, wherein immediately after the chromatography was complete, the collection disk was cooled to approximately 13 K. (without first warming it to 180 K.). The relatively ragged base line obtained in this reconstruction is believed to be the result of light scattering and excessive solvent obtained from the IR analysis. A single beam spectrum of one of the peaks of the reconstructed chromatogram shown in FIG. 3 associated with the DOWCO™ 441 butyl ester is illustrated in FIG. 4. The water and acetonitrile that has been co-deposited with the DOWCO™ 441 butyl ester on the collection disk tends to overlap and obscure the absorption bands associated with the compound of interest (i.e., the 441 butyl ester), making identification of this compound more difficult.

With Warming Procedure

Figure 5:
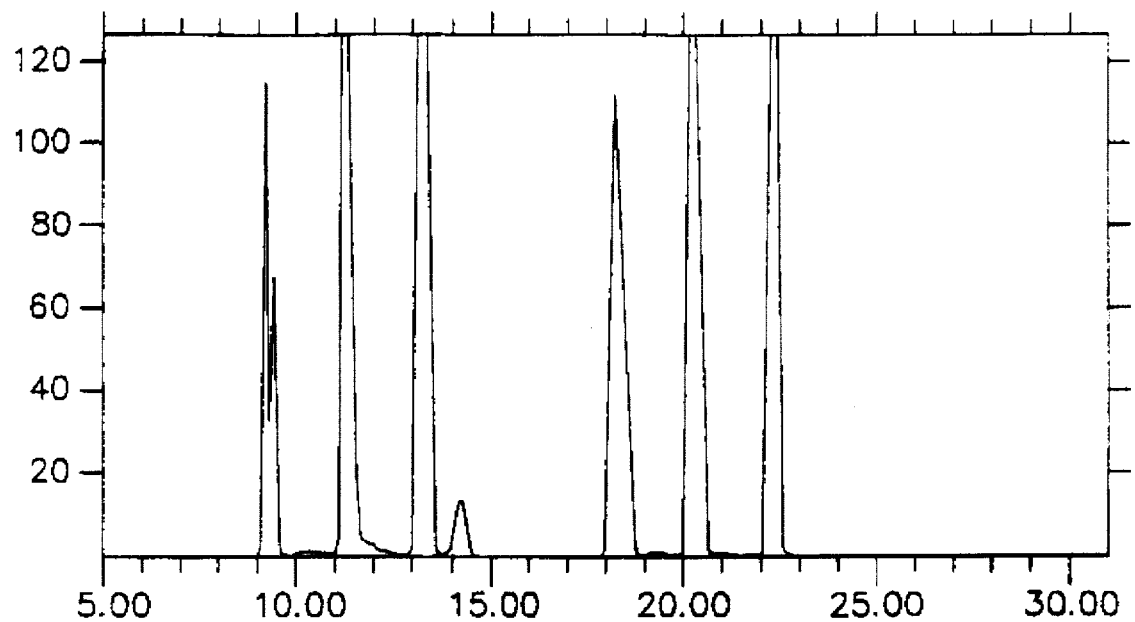
FIG. 5 is a phase sensitive IR reconstructed chromatogram of an infrared analysis of DOWCO™ butyl ester and XRD-433 1-methyl heptyl ester sample mixture where the collection disk was warmed after chromatography prior to cooling and IR analysis, wherein relative concentration is plotted on the vertical axis against retention time (in minutes) on the horizontal axis.

The same experiment was repeated altering only the post-collection process, wherein the collection disk was relatively warmed to approximately 180 K. following collection of particles, then cooled to 13 K. Observation of the collection disk following this process showed that the deposition of sample particles on the disk are more isolated and solvent free. The phase sensitive IR reconstructed chromatogram of the deposited particles is shown in FIG. 5. As is apparent, this chromatogram is essentially noise free, with the base line between analyzed components dropping to approximately zero.

A comparison of FIG. 5 to the chromatogram of FIG. 3 highlights the advantages of this modified method. It has been determined that relative warming of the disk to about 180 K. is essential to optimizing the IR analysis results, as it serves to remove residual traces of the operating solvent system from the disk and from the deposited particles.

Figure 6:
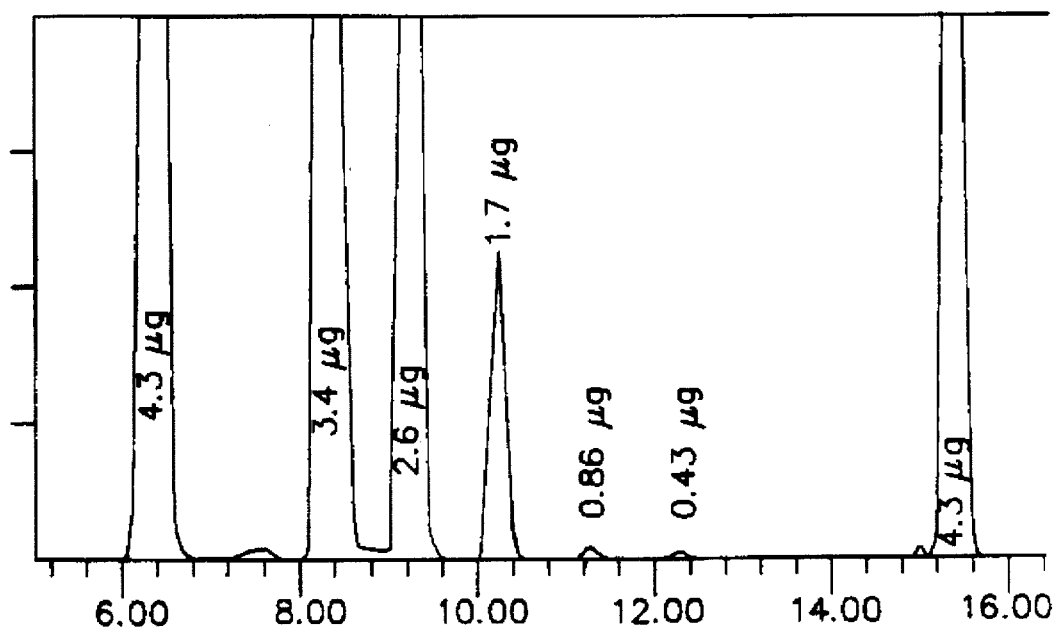
FIG. 6 is a phase sensitive IR reconstructed chromatogram of various concentrations of XRD-433 1-methyl heptyl ester, wherein relative concentration is plotted on the vertical axis against retention time (in minutes) on the horizontal axis.

A phase sensitive IR chromatogram for a series of flow injections of varying concentrations of XRD-433 1-methyl heptyl ester into the liquid chromatograph is illustrated in FIG. 6. While no generalized statement concerning the ultimate sensitivity of the present apparatus and method has been identified (since different compounds feature widely varying IR absorption characteristics), it is believed that beyond doubt, such sensitivity is superior to those obtainable utilizing previously known techniques for LC/IR analysis.

Liquid Chromatographic Separation

UV detection of separations was also undertaken utilizing the present apparatus and process. Particularly, the UV chromatogram of the separation of DOWCO™ 441 butyl ester and XRD-433 1-methyl heptyl ester injected into a $C_8$ chromatographic column is shown graphically in FIG. 7, where relative absorbance is plotted against time. The first peak is DOWCO™ 441, while the second, smaller peak is the XRD-433 compound. Similarly, the phase sensitive IR reconstructed chromatogram of the XRD-433DOWCO™ 441 mixture is shown in FIG. 8, where relative concentration of collected particles is plotted against retention time.

Figure 7:
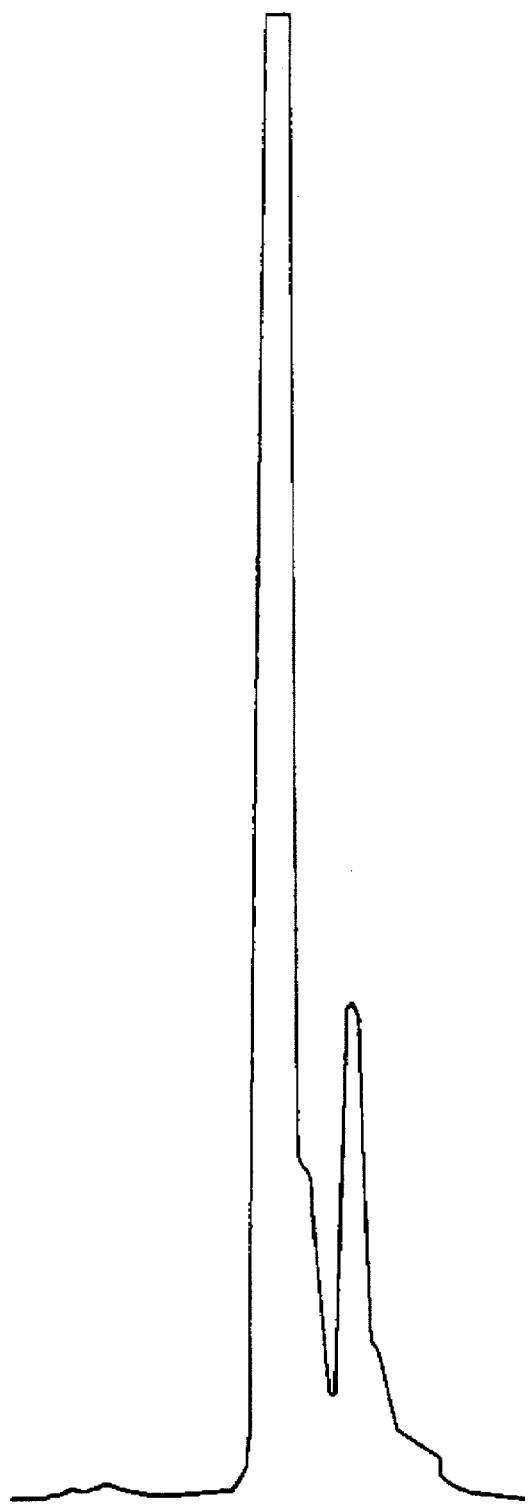
FIG. 7 is an ultraviolet (UV) chromatogram of DOWCO™ 441 butyl ester and XRD433 1-methyl heptyl ester which was injected onto a $C_8$ chromatographic column, wherein relative absorbance is plotted on the vertical axis against time on the horizontal axis.
Figure 8:
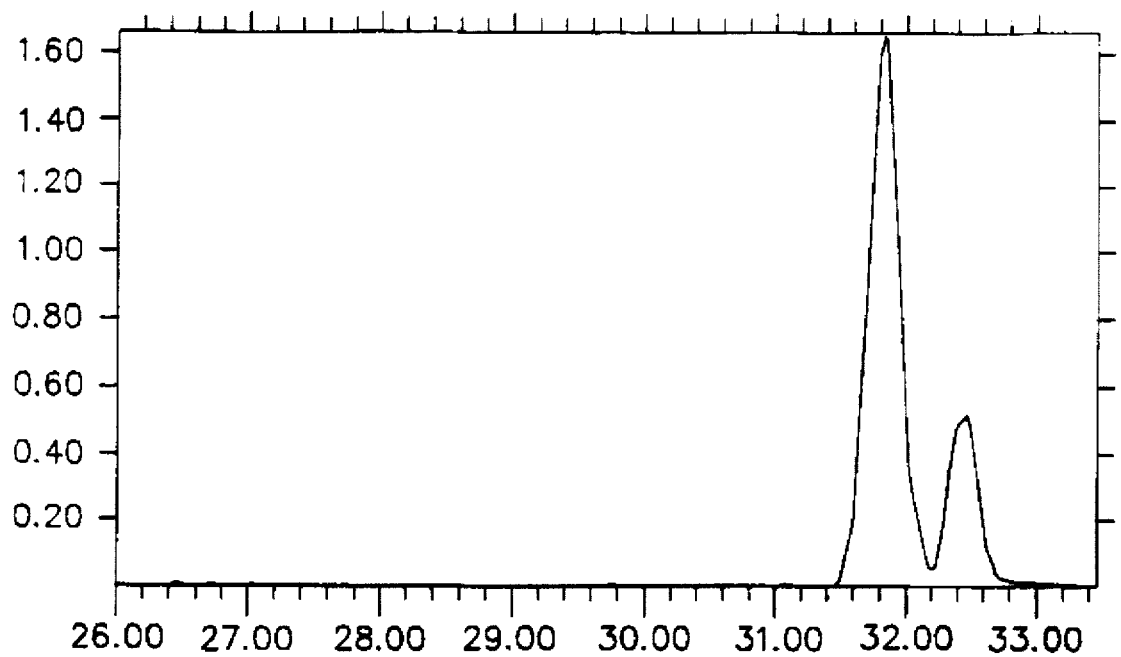
FIG. 8 is a phase sensitive IR reconstructed chromatogram of the separated mixture of FIG. 7, wherein relative concentration is plotted on the left axis against retention time (in minutes) on the horizontal axis.

A comparison of FIGS. 7 and 8 shows that the base line separation of the two components was not clearly obtained under the chromatographic conditions. However, the phase sensitive IR reconstruction of FIG. 8 indicates that the degree of separation obtained in the UV portion of the experiment is not significantly degraded by either the LC interface, or by trapping the individual components on the cryogenic collection disk.

Figure 8A:
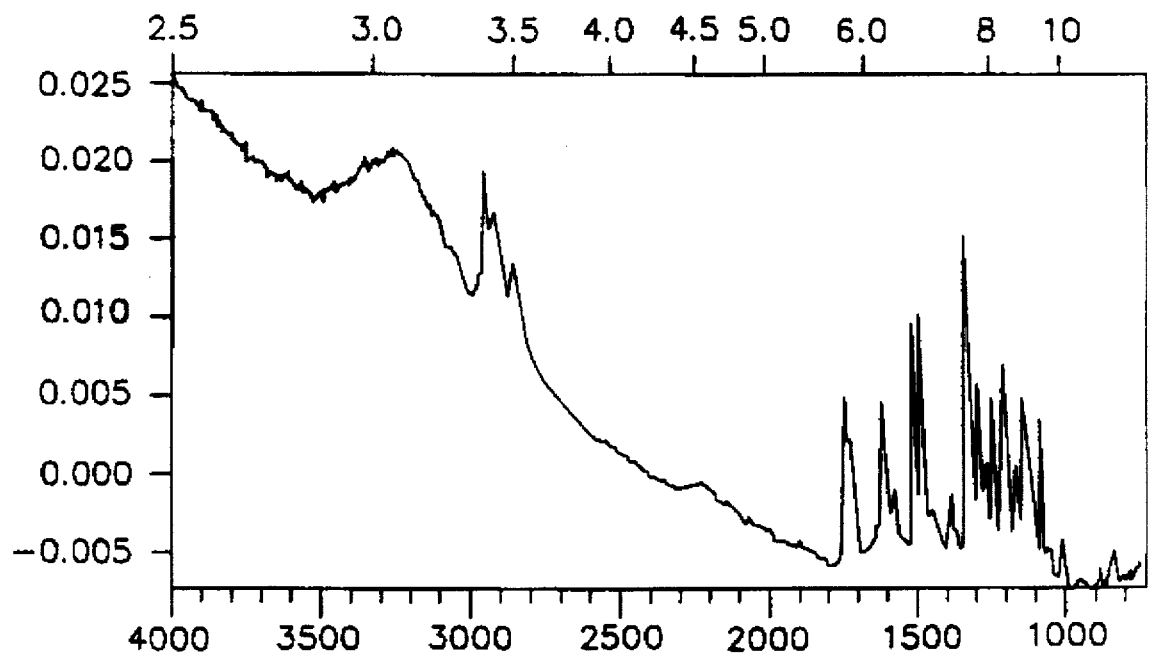
FIG. 8a illustrates an infrared spectrum obtained from chromatography of the DOWCO™ 441 Butyl Ester component of the mixture separated and illustrated in FIG. 8, wherein relative absorbance is plotted on the vertical axis against wavenumber along the lower horizontal axis, and wavelength (in microns) along the upper horizontal axis.
Figure 8B:
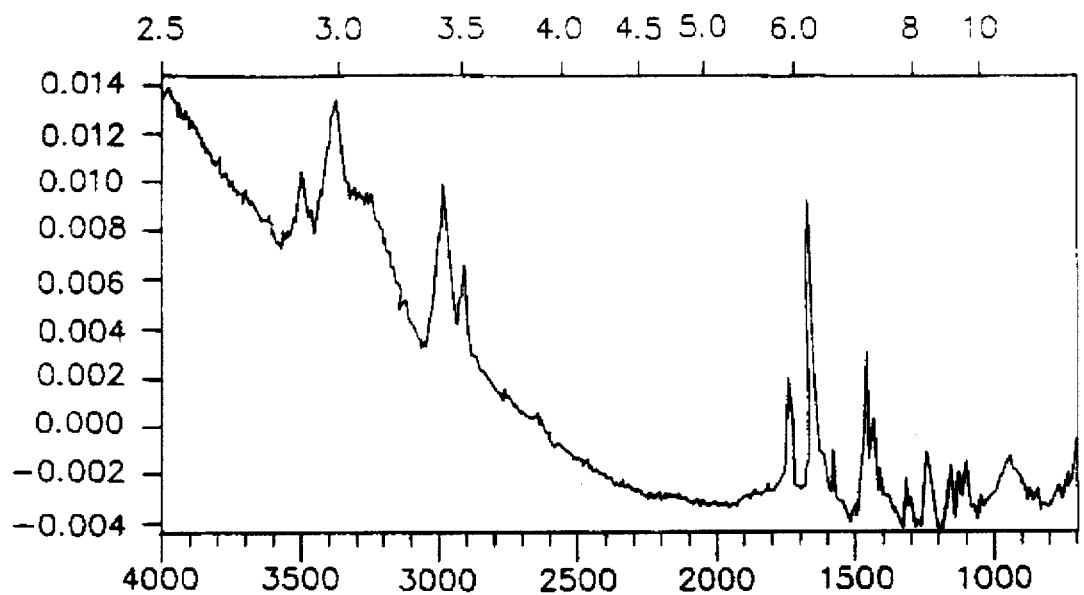
FIG. 8b illustrates an infrared spectrum obtained from chromatography of the XRD-433 1-methyl Heptyl Ester component of the mixture separated and illustrated in FIG. 8, wherein relative absorbance is plotted on the vertical axis against wavenumber along the lower horizontal axis, and wavelength (in microns) along the upper horizontal axis.

FIGS. 8a and 8b illustrate infrared spectra of the individual components DOWCO™441 Butyl Ester and XRD-433 1Methly Heptyl Ester, respectively. As can be seen in these figures, little or no spectral interferences are evident in either of these compounds.

Effects of Capillary Diameter on Sensitivity

Because it is desirable to reduce the spot size of the particles collected on the collection disk emanating from the collimating capillary tube 83 in order to optimize sensitivity and concentration, an experiment was undertaken to determine whether a capillary tube having a reduced inner diameter would favorably affect sensitivity. As set forth above, the preferred capillary inner diameter is about 1.2 mm.

Figure 9:
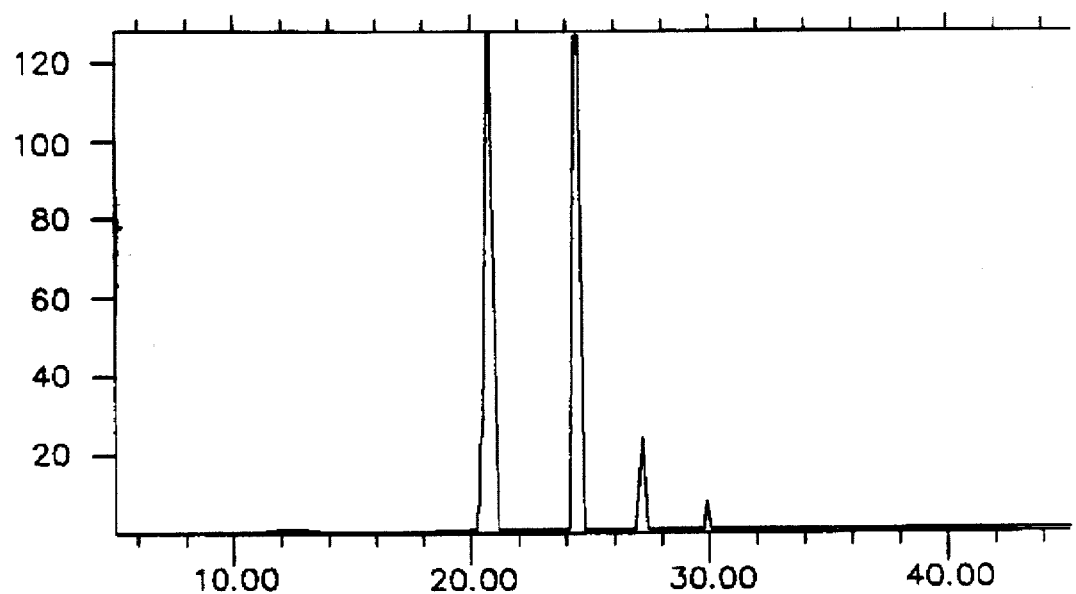
FIG. 9 is a phase sensitive IR reconstructed chromatogram of a mixture of compounds frequently used as polymer additives, utilizing a capillary inlet tube having an inside diameter of 1.2 mm, wherein relative concentration is plotted on the vertical axis against retention time (in minutes) on the horizontal axis.

A phase sensitive IR chromatogram obtained from a test mixture of compounds frequently used as polymer additives is shown in FIG. 9, where relative concentration of collected particles is plotted against retention time. The peak furthest to the left represents the individual constituent Benzyl Butylphthalate, the second peak represents Naugard XL-1, the third peak Tinuvin 328, and small peak to the right Irganox 1076. These compounds are very common and well known in the industry, and are available from a variety of sources.

Figure 10:
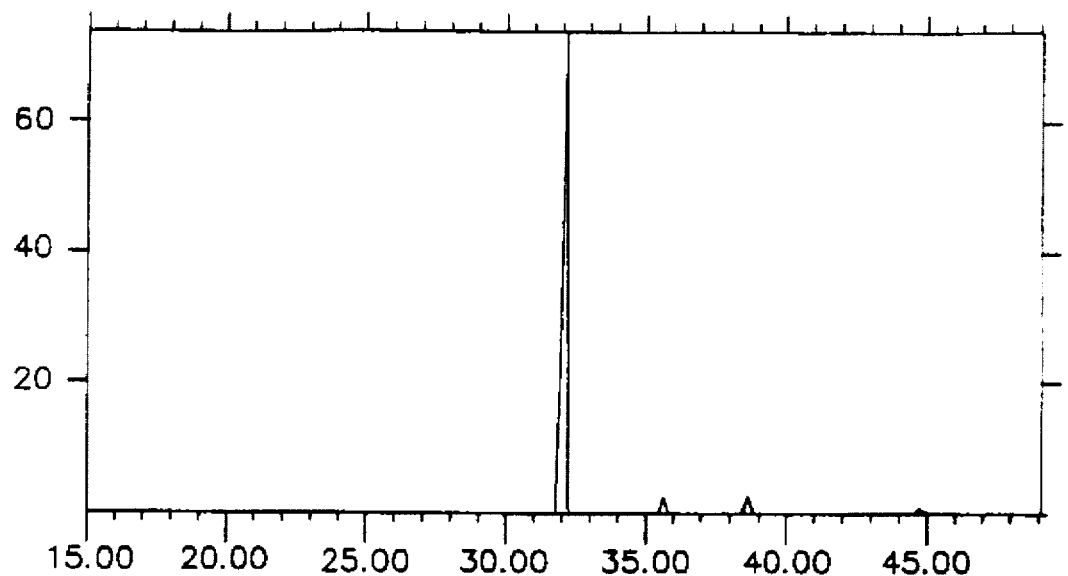

Thereafter, the 1.2 mm diameter capillary tube was replaced with a similar 1.2 mm tube having a tip inner diameter of approximately 0.5 mm. The phase sensitive IR chromatogram obtained using the 0.5 mm tipped tube with the identical mixture is shown in FIG. 10, where relative concentration of collected particles is again plotted against retention time. A comparison of FIG. 10 with FIG. 9 indicates that sensitivity was clearly lost when the smaller diameter capillary tube was used to interface the particle beam with the collection disk. Consequently, it is believed that reduction of the spot size and concentration of deposited solutes from the particle beam clearly reaches a point of diminishing returns below about 1.2 mm.

Heating of the Capillary Collimating Tube

As discussed above, if the capillary tube 83 is made of glass or a glass like material, then it is preferably heated to minimize the possibility of condensation of sample particles from the particle beam along the tube prior to deposition on the collection disk 112. A series of flow injections of XRD-433 1-methyl heptyl ester was made using the 1.2 mm capillary tube diameter operating at ambient temperatures.

The phase sensitive IR chromatogram documenting the analysis results of this example is shown in FIG. 5. Particularly, the first three concentration peaks in the nine to fourteen minute time retention period were obtained with the capillary tube being operated at ambient temperature. The fourth (smaller) peak, however, was not the result of additional sample being injected into the system. In fact, this fourth, smaller peak resulted from activation of the heating means to heat capillary tube 83 to between about 135° C and 140° C. The heating of tube 83 caused particles which had condensed or otherwise collected along tube 83 to be released and carried to collection disk 112 for deposition. Consequently, to optimize accuracy and sensitivity of the apparatus, it is preferred to heat a glass capillary tube 83 as described above.

Normal Phase Liquid Chromatography

Figure 11:
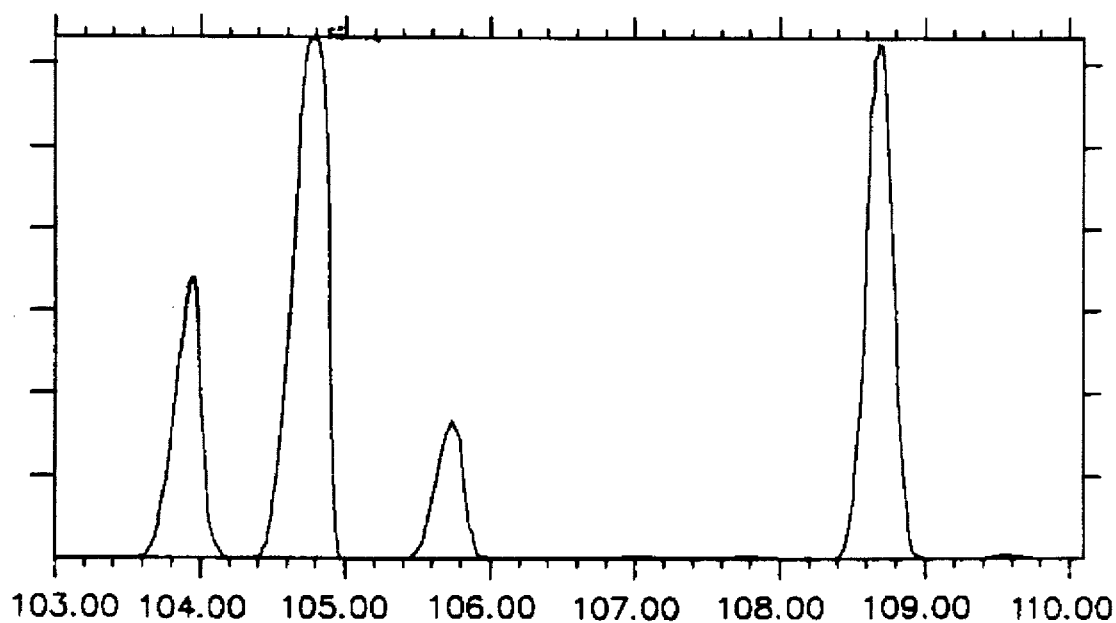
FIG. 11 is a phase sensitive IR reconstructed chromatogram of selected compounds injected into the chromatograph and processed in accordance with the present invention using THF as the solvent, wherein relative concentration is plotted on the vertical axis against retention time (in minutes) of the horizontal axis.

The phase sensitive IR reconstructed chromatogram of a mixture of selected compounds consisting of probucol and polystyrene of molecular weight 68,000 injected into the chromatograph using tetrahydrofuran (THF) as the mobile phase is shown in FIG. 11. Particularly, the first three peaks (from the left) and the sixth peak each represent probucol, while the very low blips at about times 107 and 108 represent the polystyrene. These interpretable results clearly show that the present apparatus and process is successfully applicable to reverse-phase and normal-phase liquid chromatography, with minimal solvent interference.

Size Exclusion Chromatography

Figure 12:
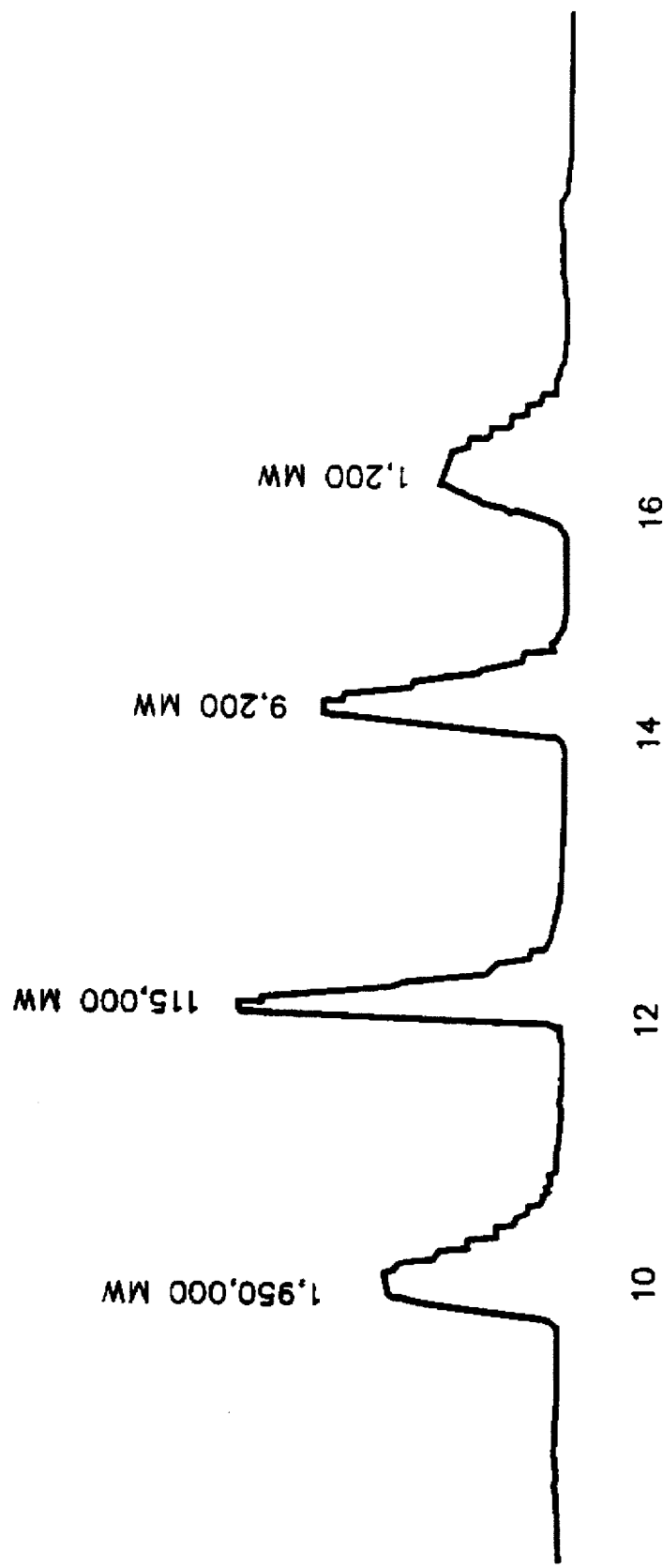
FIG. 12 is a UV chromatogram of the separation of a mixture of polystyrene molecular weight standards, wherein relative absorbance is plotted on the vertical axis against time (minutes) on the horizontal axis.

A UV chromatogram showing the results of separation of a mixture of polystyrene molecular weight standards is illustrated in FIG. 12. These polystyrene molecular weight standards are available in the industry, such as from Polymer Laboratories Inc., of Amherst, Mass. Particularly, the peak shown near the ten minute retention time is molecular weight 1,950,000, that shown near the 12-minute interval is 115,000 molecular weight, that shown just beyond the 14-minute time period is 9,200 molecular weight, and 1,200 molecular weight shown at just beyond 16 minutes.

Figure 13:
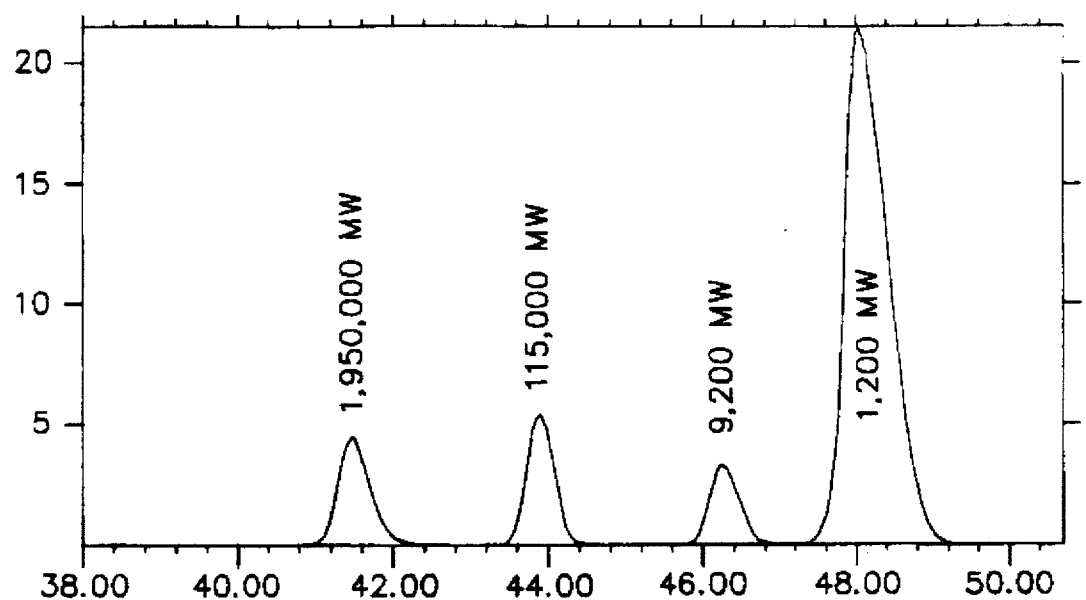
FIG. 13 is a phase sensitive IR reconstructed chromatogram of a mixture of polystyrene molecular weight standards, wherein relative concentration is plotted on the vertical axis against retention time (in minutes) on the horizontal axis.
Figure 13A:
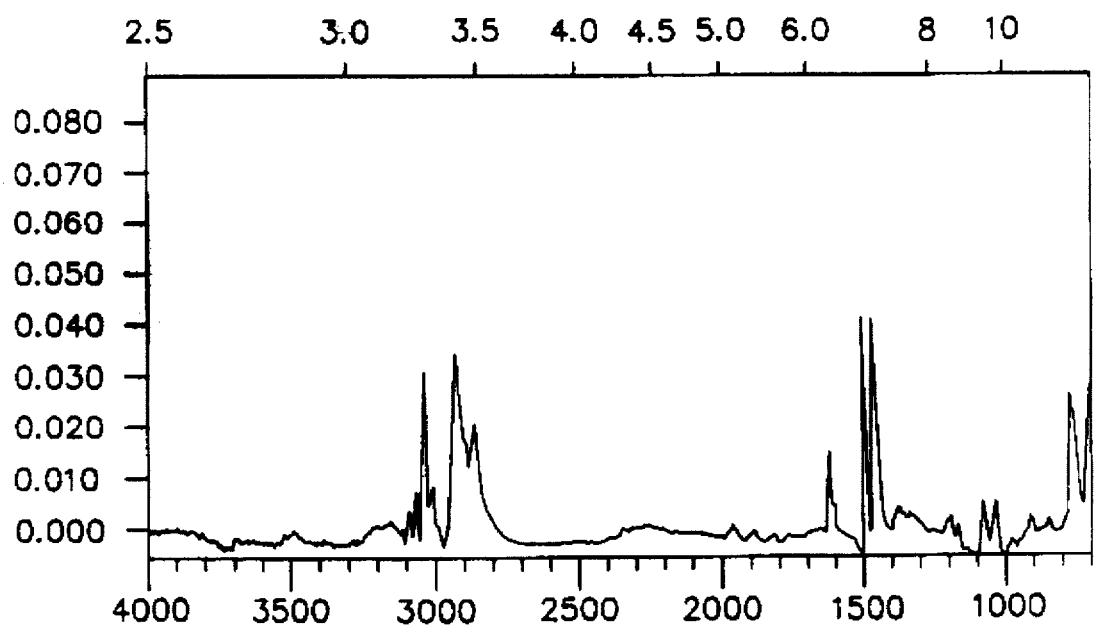
FIG. 13a illustrates an infrared spectrum obtained from chromatography of the 1,950,000 molecular weight polystyrene component of the mixture of polystyrene molecular weight standards separated and illustrated in FIG. 13, wherein relative absorbance is plotted on the vertical axis against wavenumber along the lower horizontal axis, and wavelength (in microns) along the upper horizontal axis.
Figure 13B:
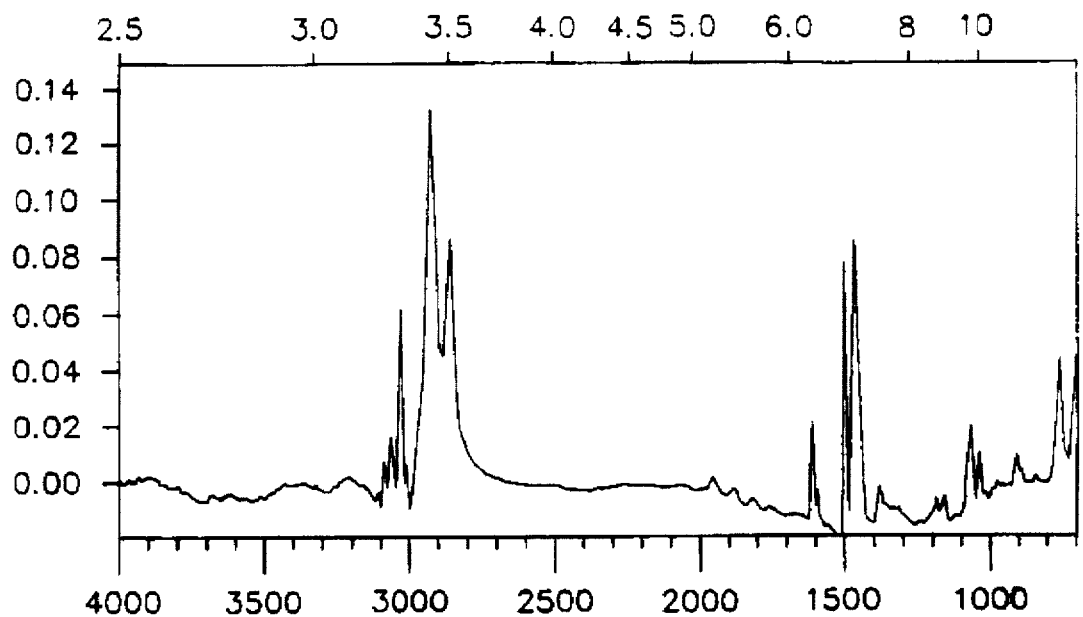
FIG. 13b illustrates an infrared spectrum obtained from chromatography of the 1,200 molecular weight polystyrene component of the mixture of polystyrene molecular weight standards separated and illustrated in FIG. 13, wherein relative absorbance is plotted on the vertical axis against wavenumber along the lower horizontal axis, and wavelength (in microns) along the upper horizontal axis.

The UV detector was set at 265 microns. The corresponding phase sensitive IR chromatogram for this experiment is shown in FIG. 13, wherein the first two concentration peaks from the left represent the 1,950,000 and 115,000 molecular weight constituents, respectively, the third peak at 46 minutes is 9,200 molecular weight, while the fourth peak at about 48 minutes is the 1,200 molecular weight constituent. The IR chromatogram clearly indicates that the separation of the four standards is maintained through the membrane separator and particle beam deposition process of the present invention, and it is also apparent that even the high molecular weight polystyrene sample is collected on the cryogenic collection disk. FIGS. 13a and 13b illustrate infrared spectra of the 1,950,000 molecular weight and 1,200 molecular weight polystyrene components, and are representative of the mixture discussed above.

Figure 14:
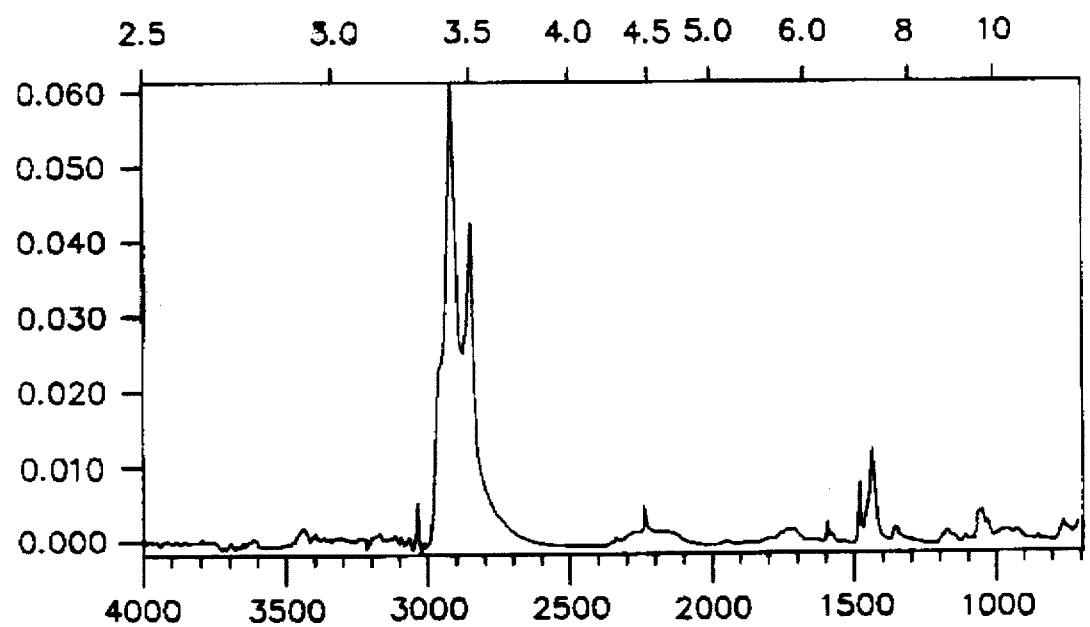
FIG. 14 illustrates the infrared spectrum obtained from chromatography of a 1200 molecular weight styrene/acrylonitrile copolymer wherein relative absorbance is plotted on the vertical axis against wavenumber along the lower horizontal axis, and wavelength (in microns) along the upper horizontal axis.

Similarly, the IR spectrum obtained from chromatographing a 1200 molecular weight styrene/acrylonitrile copolymer is shown in FIG. 14, where relative absorbance is plotted along the vertical axis, wavenumber is plotted along the lower horizontal axis, and wavelength (in microns) is plotted along the upper horizontal axis. As can be appreciated, this plot clearly indicates the potential for utilizing the present apparatus and process for determining the composition of SAN copolymers based upon relative molecular weight. As will be understood, infrared analysis of systems separated by size exclusion chromatography will allow the determination of the composition of various polymer systems with respect to varying molecular weights, in addition to allowing the study and determination of composition of various fractions of polymer blends that have been separated by size exclusion chromatography. The present apparatus and process can also be readily interfaced with hydrodynamic chromatography and field flow fractionation chromatography, which will enable the accurate determination of composition of polymer species with respect to particle size.

Having shown and described the preferred embodiments of the present invention, further adaptions of the interface and particle collection apparatus and process described herein can be accomplished by appropriate modifications by one of ordinary skill in the art without departing from the scope of the present invention. Accordingly, the scope of this invention should be considered in terms of the following claims and is understood not to be limited to the details of structure and operation shown and described in the specification and drawings.

What is claimed is:

1. Apparatus for interfacing a liquid chromatograph with a spectrometer, the liquid chromatograph having an eluant, the eluant containing a solvent and a component of interest, the apparatus comprising:
   (a) means for generating a stream of droplets of the eluant;
   (b) means for removing most of the solvent from the stream of droplets of the eluant to thereby generate a stream of particles, the particles containing the component of interest and any residual solvent;
   (c) a cryogenic surface;
   (d) means for focusing the stream of particles onto the cryogenic receiving surface so that the particles adhere to the cryogenic receiving surface wherein the gap between the means for focusing the stream of particles onto the cryogenic receiving surface and the cryogenic receiving surface is between about one-eighth and about one millimeter; and
   (e) means for directly controlling the temperature of the cryogenic receiving surface at a temperature at least as low as two hundred and fifty degrees Kelvin.

2. The apparatus of claim 1, wherein the gap between the means for focusing the stream of particles onto the cryogenic receiving surface and the cryogenic receiving surface is between about one-quarter and about one half millimeter.

3. The apparatus of claim 2, wherein the means for focusing the stream of particles onto the cryogenic receiving surface is selected from the group consisting of a capillary tube and an aperture plate.

4. The apparatus of claim 3, wherein the means for focusing the stream of particles onto the cryogenic receiving surface is a capillary tube having an internal diameter of between about one-half and about two millimeters.

5. The apparatus of claim 4, wherein the capillary tube has an internal diameter of between about one and about one and one-half millimeters.

6. The apparatus of claim 1, wherein the means for focusing the stream of particles onto the cryogenic receiving surface is selected from the group consisting of a capillary tube and an aperture plate.

7. The apparatus of claim 6, wherein the means for focusing the stream of particles onto the cryogenic receiving surface is a capillary tube having an internal diameter of between about one-half and about two millimeters.

8. The apparatus of claim 7, wherein the capillary tube has an internal diameter of between about one and about one and one-half millimeters.

9. A method for interfacing a liquid chromatograph with a spectrometer, the liquid chromatograph having an eluant, the eluant containing a solvent and a component of interest, the method comprising the steps of:
   (a) generating a stream of droplets of the eluant;
   (b) removing most of the solvent from the stream of droplets of the eluant to generate a stream of particles, the particles containing the component of interest;
   (c) focusing the stream of particles onto a cryogenic receiving surface directly maintained at a temperature effective to cause the particles to adhere to the cryogenic receiving surface thereby forming a region of adhered particles, the temperature being less than two hundred and fifty degrees Kelvin; and
   (d) warming the cryogenic receiving surface to a temperature effective to volatilize essentially all of any residual solvent from the region of adhered particles prior to spectroscopic analysis of the region of adhered particles.

10. The method of claim 9, wherein in step (c) the temperature of the cryogenic surface is maintained between about seventy and about one hundred and five degrees Kelvin, wherein in step (d) the cryogenic surface is warmed to a temperature of between about one hundred and five and about two hundred degrees Kelvin.

* * * * *